(12) United States Patent
Babilo et al.

(10) Patent No.: US 10,005,927 B2
(45) Date of Patent: Jun. 26, 2018

(54) THERMALLY CONDUCTIVE FLEXIBLE ADHESIVE FOR AEROSPACE APPLICATIONS

(71) Applicant: The Boeing Company, Chicago, IL (US)

(72) Inventors: Peter Babilo, Mission Viejo, CA (US); Randall Jay Moss, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 31 days.

(21) Appl. No.: 15/258,073

(22) Filed: Sep. 7, 2016

(65) Prior Publication Data

US 2016/0376477 A1    Dec. 29, 2016

Related U.S. Application Data

(62) Division of application No. 14/189,302, filed on Feb. 25, 2014, now Pat. No. 9,464,214.

(51) Int. Cl.
*C09J 11/06* (2006.01)
*C08K 3/38* (2006.01)
(Continued)

(52) U.S. Cl.
CPC .......... *C09J 11/06* (2013.01); *B29C 65/4855* (2013.01); *B32B 37/1284* (2013.01);
(Continued)

(58) Field of Classification Search
CPC ...................................................... C09J 11/06
See application file for complete search history.

(56) References Cited

U.S. PATENT DOCUMENTS 8,288,466 B2   10/2012  Lin et al.
9,464,214 B2 * 10/2016  Babilo .................. C09J 163/00
(Continued)

FOREIGN PATENT DOCUMENTS

EP      2257610        12/2010
JP      10060398 A      3/1998
(Continued)

OTHER PUBLICATIONS

"U.S. Appl. No. 14/189,302, Examiner Interview Summary dated Jun. 28, 2016", 1 pg.
(Continued)

*Primary Examiner* — Daniel H Lee
(74) *Attorney, Agent, or Firm* — Kwan & Olynick LLP

(57) ABSTRACT

Provided are methods of forming thermally conductive flexible bonds for use in electronic boards of unmanned spacecrafts and other types of aircraft. Also provided are methods of preparing adhesive materials to form these bonds including methods of preparing treated filler particles. In some aspects, an adhesive material includes filler particles having organofunctional groups, such as boron nitride particles treated in silane. These particles may be combined with a urethane modified epoxy to form the adhesive material. The weight ratio of the particles in the adhesive material may be about 40-60%. The adhesive material may be thermally cured using a temperature of less than 110° C. to prevent damage to bonded electronic components. The cured adhesive may have a thermal conductivity of at least about 2 W/m K measured in vacuum and may have a glass transition temperature if less than −40° C.

14 Claims, 7 Drawing Sheets

(51) Int. Cl.
*C09J 163/00* (2006.01)
*H05K 1/02* (2006.01)
*H05K 3/30* (2006.01)
*B32B 37/12* (2006.01)
*B32B 37/18* (2006.01)
*C09K 5/14* (2006.01)
*C09J 5/06* (2006.01)
*C09J 9/00* (2006.01)
*B29C 65/48* (2006.01)
*C07F 7/18* (2006.01)
*C08K 9/06* (2006.01)
*B29K 63/00* (2006.01)
*B29K 509/04* (2006.01)
*B29L 31/34* (2006.01)

(52) U.S. Cl.
CPC ............ *B32B 37/18* (2013.01); *C07F 7/1836* (2013.01); *C08K 3/38* (2013.01); *C08K 9/06* (2013.01); *C09J 5/06* (2013.01); *C09J 9/00* (2013.01); *C09J 163/00* (2013.01); *C09K 5/14* (2013.01); *H05K 1/0203* (2013.01); *H05K 3/305* (2013.01); *B29K 2063/00* (2013.01); *B29K 2509/04* (2013.01); *B29L 2031/3406* (2013.01); *B32B 2037/1253* (2013.01); *B32B 2457/00* (2013.01); *C08K 2003/382* (2013.01); *C09J 2203/326* (2013.01); *C09J 2463/00* (2013.01); *H05K 2201/0133* (2013.01); *H05K 2201/0209* (2013.01); *H05K 2201/0239* (2013.01); *H05K 2203/12* (2013.01); *Y02P 70/613* (2015.11)

(56) References Cited

U.S. PATENT DOCUMENTS

| | | |
|---|---|---|
| 2001/0004131 A1 | 6/2001 | Masayuki et al. |
| 2007/0041918 A1 | 2/2007 | Meneghetti et al. |
| 2010/0167002 A1 | 7/2010 | Chu et al. |
| 2011/0290468 A1 | 12/2011 | Nakayama et al. |
| 2015/0240132 A1 | 8/2015 | Babilo et al. |

FOREIGN PATENT DOCUMENTS

| | | |
|---|---|---|
| WO | 2009120376 A2 | 10/2009 |
| WO | 2013172429 A1 | 11/2013 |

OTHER PUBLICATIONS

"U.S. Appl. No. 14/189,302, Non Final Office Action dated Mar. 17, 2016", 9 pgs.

"U.S. Appl. No. 14/189,302, Notice of Allowance dated Jun. 28, 2016", 10 pgs.

"U.S. Appl. No. 14/189,302, Restriction Requirement dated Jan. 22, 2016", 5 pgs.

"Canadian Application Serial No. 2,878,529, Office Action dated Jan. 25, 2016", 3 pgs.

"European Application Serial No. 15151072.4, Search Report dated Jul. 2, 2015", 11 pgs.

Kim, Kiho et al., "Chemically modified boron nitride-epoxy terminated dimethylsiloxane composite for improving the thermal conductivity", Ceramics International 40, 2014, pp. 2047-2056.

Liotine, Frank J., "Thermal Management Performance and Attachment Reliability Using Urethane Film Adhesives", Retrieved from the Internet: :http://www.apteklabs.comjarticles/APTEK%20-%20Thermal%20Management%20Article.pdf, Accessed on Jun. 24, 2015, 2000, 6 pgs.

Wattanakul, Karnthidaporn et al., "Effective Surface Treatments for Enhancing the Thermal Conductivity of BN-Filled Epoxy Composite", Journal of Applied Polymer Science, vol. 119, 2010, pp. 3234-3243.

Xu, Yunsheng et al., "Increasing the Thermal Conductivity of Boron Nitride and Aluminum Nitride Particle Epoxy-Matrix Composites by Particle Surface Treatments", Composite Interfaces, vol. 7, No. 4, 2000, pp. 243-256.

* cited by examiner

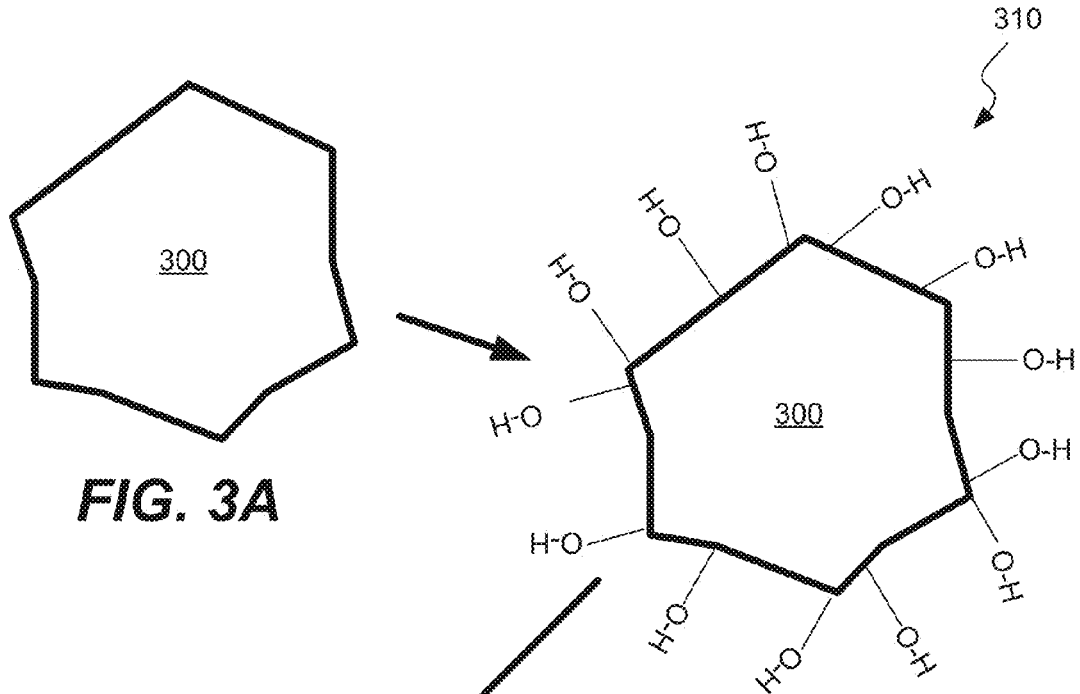
*FIG. 3A*
*FIG. 3B*
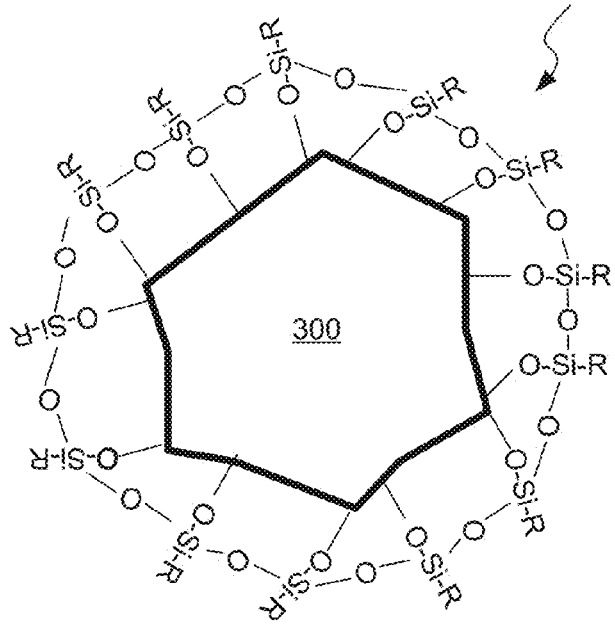
*FIG. 3C*

THERMALLY CONDUCTIVE FLEXIBLE ADHESIVE FOR AEROSPACE APPLICATIONS

CROSS-REFERENCE TO RELATED APPLICATIONS

This application is a divisional application claiming priority to U.S. application Ser. No. 14/189,302, entitled "THERMALLY CONDUCTIVE FLEXIBLE ADHESIVE FOR AEROSPACE APPLICATIONS," filed on Feb. 25, 2014, which is incorporated herein by reference in their entirety for all purposes.

BACKGROUND

Thermal management of electronic components and electronic boards including these components is essential to the successful operation of various aerospace vehicles, such as unmanned spacecrafts. The continued miniaturization of the electronic components and integration schemes resulted in a dramatic increase of heat generated per unit volume. This increased heat generation not only limits the design of the circuit (e.g., the layout of electronic components on a board) and limits the design of individual electronic components but also jeopardizes the reliability of the overall circuit and individual components due to overheating of the components, connections, conductive lines, and other features of the electronic boards.

The heat generated during operation of these electronic components needs to be transferred to other areas to ensure continuous operations of the components. Because the boards often operate in vacuum environments, such as in unmanned spacecrafts, the heat may be primarily transferred through direct physical contact between various components, which may be referred to as conductive heat transfer. Specifically, the heat is transferred from components to a board supporting these components, then from the board to a chassis, and then from the chassis to a frame and other major components of the unmanned spacecraft.

Thermally conductive adhesives are often used to enhance the heat transfer between electronic components and boards supporting these components. A high thermal conductivity of these adhesives is essential for fast heat dissipation from the component and thermal management of the overall board. Currently available adhesives that meet specific requirements for space applications have a thermal conductivity of only up to 0.6 W/mK. These adhesives use $Al_2O_3$ (alumina) as a conductive filler suspended in an epoxy or polyurethane resin. Best thermally conductive but electrically insulative adhesives, which are not space compatible, have a thermal conductivity of only about 1 W/mK. These adhesives employ a combination of alumina, boron nitride, and/or aluminum nitride as a conductive filler suspended in an epoxy, polyurethane or silicone resin.

It should be noted that these values of thermal conductivity are based on measurements of a bonded joint configuration in a vacuum, which may be viewed as a modified ASTM C 177 test method performed in vacuum. Specifically, an adhesive material is used to bond two aluminum plates, and the heat flux between these plates is measured to determine the thermal conductivity value of the adhesive material. This method is believed to be the most representative of heat transfer between electronic components and boards supporting these components.

Other approaches used to measure a thermal conductivity include laser scanning of a free standing sample (e.g., a puck looking cylinder). The values obtained from these other measurement techniques are often different or, more specifically, larger than values obtained using the bonded joint configuration in vacuum, often 2-50 times larger. Furthermore, these other measurement techniques are not performed in vacuum resulting in artificially higher thermal conductivity values caused by additional heat losses through the air.

SUMMARY

Provided are methods of forming thermally conductive flexible bonds for use in electronic boards of unmanned spacecrafts and other types of aircraft. Also provided are methods of preparing adhesive materials to form these bonds including methods of preparing treated filler particles. In some aspects, an adhesive material includes filler particles having organofunctional groups, such as boron nitride particles treated in silane. These particles may be combined with a urethane modified epoxy to form the adhesive material. The weight ratio of the particles in the adhesive material may be about 40-60%. The adhesive material may be thermally cured using a temperature of less than 110° C. to prevent damage to bonded electronic components. The cured adhesive may have a thermal conductivity of at least about 2 W/m K measured in vacuum and may have a glass transition temperature of less than −40° C.

In some aspects, a method of forming a thermally conductive flexible bond for use in an electronic board involves providing one or more adhesive components. The one or more adhesive components may include boron nitride particles having organofunctional groups attached to the surface of these particles. Furthermore, the one or more adhesive components may include a urethane modified epoxy. The urethane modified epoxy may be already premixed with the boron nitride particles and no further mixing may be needed. For example, the one or more adhesive components may be provided as a frozen premix of the urethane modified epoxy and the boron nitride particles. Alternatively, the urethane modified epoxy and the boron nitride particles may be provided as separate components and mixed together during one of the later operations.

The method may proceed with forming an adhesive material from the one or more adhesive components. This forming operation may involve warming up a frozen premix (a single frozen component) to an operating temperature or mixing multiple components to form the adhesive material. The adhesive material may be then applied onto a surface of the electronic board by hand or by use of an automated dispensing system and a contact may be formed between an electronic component and the adhesive material applied to the surface of the electric board. In some aspects, the adhesive material may be first applied to an electronic component and then placed onto an electronic board.

The process may continue with curing the adhesive material, which forms a cured adhesive structure between the electric board and the electronic component. The cured adhesive structure provides the thermally conductive flexible bond between the electric board and the electronic component. The flexibility, low glass transition temperature and low coefficient of thermal expansion of the cured adhesive structure prevents damage to the electric board and the electronic component when the assembly undergoes temperature changes (e.g., caused by the operation of the electronic component) or when the electronic component needs to be replaced.

In some aspects, the concentration of the boron nitride particles in the adhesive material is between about 20% by weight and 70% by weight or, more specifically, between about 40% by weight and 60% by weight. Likewise, the concentration of the boron nitride particles in the cured adhesive structure between about 40% by weight and 60% by weight as no materials may be added or removed from the adhesive material when it is cured. The cured adhesive structure may have a thermal conductivity of at least about 2 W/m-K or, more specifically, of at least about 3 W/m-K. Furthermore, the cured adhesive structure may have a glass transition temperature of less than about −40° C. or, more specifically, less than about −60° C. such as about −70° C. The cured adhesive material may have a shear strength of between about 100 psi and 500 psi. In some embodiments, the cured adhesive structure has a tensile modulus of between about $10^3$ psi and $10^5$ psi. Furthermore, the cured adhesive has a weight loss of less than about 1% during outgassing.

The curing operation may be performed at a temperature of less than 110° C. such as about 100° C. At these low temperatures, the thermal damage to electronic components attached to the board is reduced. The duration of the curing operation may be between about 30 minutes and 120 minutes, such as about 60 minutes. The cured adhesive structure may have an average thickness of between about 0.001 inches and 0.010 inches between the electric board and the electronic component. The cured adhesive structure needs to be relatively thin to ensure low thermal resistance. Yet, the cured adhesive structure needs to physically contact both the electronic component and the board and its thickness may be driven by the spacing between electronic component and the board.

Also provided is a method of preparing a thermally conductive flexible adhesive or, more specifically, a method of preparing silane treated filler particles. In some aspects, this method involves providing boron nitride particles. The average aspect ratio between any two dimensions of the boron nitride particles may be less than 5. Such boron nitride particles may be defined as three dimensional particles with no dimensions being substantially larger (e.g., more than 5 times) than any other dimensions. In some aspects, the average particle size of the boron nitride particles is between 10 micrometers and 200 micrometers.

The method may proceed with attaching hydroxyl groups to the surface of the boron nitride particles. The boron nitride particles having the hydroxyl groups on their surface are then exposed to a solution having silane. The silane may have organofunctional groups, such glycidyl groups or methoxy groups. The silane attaches to the surface of the boron nitride particles. The method may proceed with washing the boron nitride particles to remove residual silane not bound to these particles. Examples of suitable silanes include (3-glycidyloxypropyl)trimethoxysilane, [3-(2-Aminoethylamino)propyl]-trimethoxysilane, and (3-Trimethoxysilylproyl)-diethylenetriamine.

In some aspects, the solution containing the silane has a pH level of between about 5 and 6. The weight ratio of the silane to boron nitride particles is between 2% by weight and 3% by weight. The concentration of the silane in the solution may be between about 0.08% by weight and 0.35% by weight.

Also provide is a method of preparing a thermally conductive flexible adhesive material. The method may involve providing a urethane modified epoxy and combining the urethane modified epoxy with boron nitride particles thereby forming a combined material. The concentration of the boron nitride particles in the combined material may be between about 20% by weight and 70% by weight or, more specifically, between about 40% by weight and 60% by weight. The boron nitride particles may include organofunctional groups attached to a surface of the boron nitride particles. The method may proceed with mixing the combined material to form the thermally conductive flexible adhesive material. The mixing may be performed using a dual asymmetric centrifugal mixer. The thermally conductive flexible adhesive material may have a viscosity of at least about 100,000 cP after mixing. In some aspects, the method also involves freezing the thermally conductive flexible adhesive. Furthermore, prior to combining the urethane modified epoxy with the boron nitride particles, the method may involve mixing a base resin of the urethane modified epoxy with a hardener of the urethane modified epoxy.

Provided also a thermally conductive flexible adhesive material including a urethane modified epoxy and boron nitride particles or some other filler particles listed below. The concentration of the boron nitride particles or other filler particles may be between about 40% by weight and 60% by weight. In some embodiments, the boron nitride particles or other filler particles include organofunctional groups attached to the surface of the particles. The thermally conductive flexible adhesive material may be provided as a frozen premix or a kit of different components ready for mixing, e.g., using a dual asymmetric centrifugal mixer. Prior to the application, the frozen premix may be brought to the room temperature or the kit may be mixed. In some embodiments, the base resin and the hardener of the urethane modified epoxy provided in the kit are mixed together prior to introducing the boron nitride particles into the mixture. In the ready for application state, the thermally conductive flexible adhesive material may have a viscosity of at least about 100,000 cP after mixing.

These and other aspects are described further below with reference to the figures.

BRIEF DESCRIPTION OF THE DRAWINGS

FIG. 3A-3C are schematic illustrations of filler particles at different stages of the treatment process, in accordance with some aspects.

DETAILED DESCRIPTION

Figure 1:
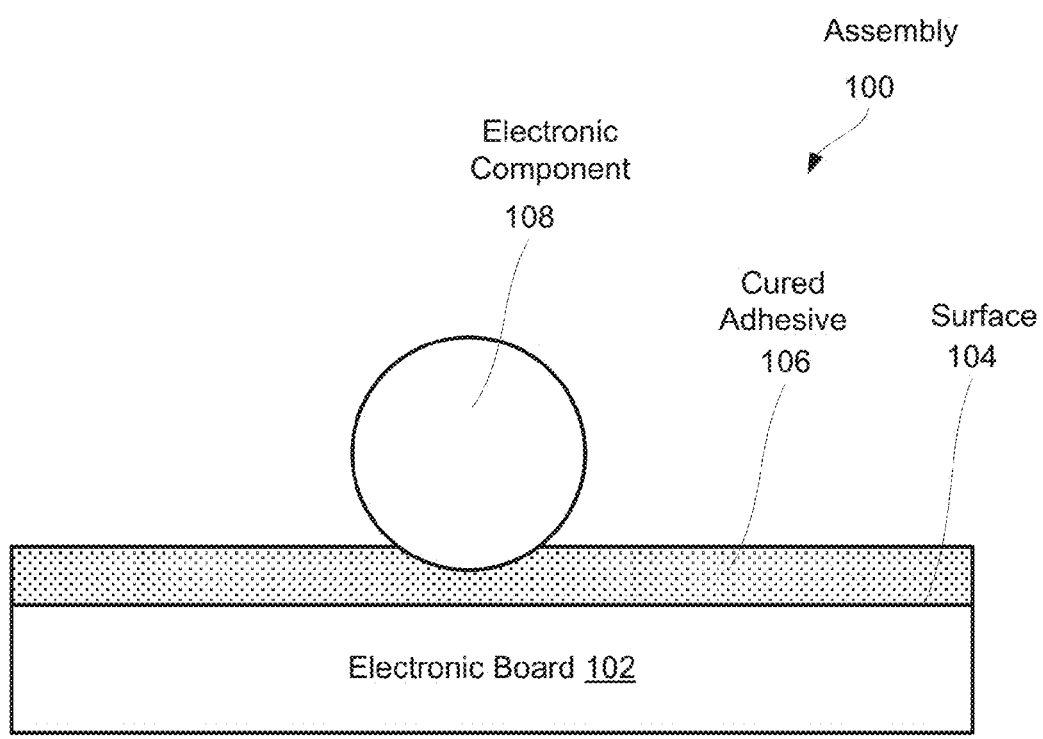
FIG. 1 is a schematic illustration of an assembly including a thermally conductive flexible adhesive bonding an electronic component to the surface of an electronic board of an unmanned spacecraft, in accordance with some aspects.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific aspects, it will be understood that these aspects are not intended to be limiting.

Introduction

As noted above, electronic components of aircraft and spacecraft often operate in specific environments and/or operating conditions, which create challenges in thermal management of these components. For example, unmanned spacecrafts operate predominantly in vacuum environments and have wide operating temperature ranges. As such, electronic components of these unmanned spacecrafts heavily rely on adhesives provided between these components and electronic boards supporting these components for heat dissipation. As such, a high thermal conductivity is essential for unmanned spacecraft applications and other aerospace applications. However, as also noted above, most of space-grade adhesives have a thermal conductivity of only up to 0.6 W/mK, which significantly restricts design of electronic circuits. In addition to high thermal conductivities, space-grade and other types of aerospace adhesives often need to be electrically insulating, have low glass transition temperatures (e.g., lower than their operating temperature ranges), be sufficiently flexible to accommodate different coefficients of thermal expansion and temperature fluctuations, and have substantially no outgassing during their operation (e.g., in the vacuum environment and/or at large temperature variations). Each of these properties will now be described with reference to spacecraft applications. However, one having ordinary skills in the art would understand that the described adhesive materials and methods of preparing these adhesives and using these adhesives to form thermally conductive flexible bonds may be used for other aerospace applications. For example, some aircraft applications require adhesive materials with high thermal conductivities.

An adhesive material used to support an electronic component on a board often contacts different connecting terminals of this component as well as connecting terminals of various other electronic components provided on the same board. For example, the adhesive material may be applied as a layer extending over the entire surface of the board and making contacts with all or most components on this board and, more specifically, with their electrical connecting terminals. As such, the adhesive material uses for such applications needs to be electrically insulating. For purposes of this disclosure, an adhesive is deemed to be electrically insulating when its resistivity is at least about $10^{10}$ Ohm-cm. Yet, a combination of a high electrical resistivity and a high thermal conductivity is hard to achieve in the same material. Usually, materials with a high thermal conductivity are also good electrical conductors. For example, carbon-based materials are often used in thermally conductive adhesives, but these adhesives also tend to be electrically conductive and may short the circuit.

Furthermore, for an adhesive material to be electrically insulating, each of its main components, such as an epoxy and filler particles, needs to be sufficiently insulating. Boron nitride, aluminum nitride, and other like materials are suitable filler particles as their electrical resistivity is typically greater than about $10^{14}$ Ohm-cm. At the same time, boron nitride and aluminum nitride have relatively high thermal conductivity as noted below. Finding a suitable electrically binding agent is generally simpler.

Furthermore, space-grade adhesives generally need to have a very low glass transition temperature, such as less than about −40° C. or even less than about −50° C., such as about −70° C. Most commercially available thermally conductive adhesives have relatively high glass transition temperatures, such as between +30° C. and +50° C. Such high glass transition temperatures are typically due to very high operating temperatures of these adhesives. However, unmanned spacecraft have much wider operating range than many other applications. In some aspects, an unmanned spacecraft temperature range is between about −30° C. and +100° C. When a material goes through a glass transition, it may generate significant stress on bonded components causing various defects. As such, the glass transition temperature of an adhesive needs to be outside of the operating range. More specifically, the glass transition temperature of an adhesive may need kept below this operating range. As such, most commercially available thermally conductive adhesives are not applicable for unmanned spacecraft and other aerospace applications.

Another characteristic of space-grade adhesives is flexibility to prevent excessive stresses on electronic components and a board, in particularly due to major temperature swings often associated with aerospace applications and different coefficients of thermal expansion of bonded materials. These stresses can damage the electronic components, the board, and the connections causing cracking and other inconsistencies. At the same time, flexibility needs to be limited to ensure mechanical support to the bonded component. Flexibility may be characterized by a tensile modulus and shear stress. For example, a suitable tensile modulus may be about $10^3$ psi and $10^5$ psi for unmanned aircraft and other aerospace applications. The shear strength of a suitable adhesive material may be between about 100 psi and 500 psi. These levels of the shear strength also allow removing and replacing components (e.g., reworking an assembly after the adhesive material is cured) without damaging the electronic board and other components that remain on the board.

Adhesive materials used for electronic boards of unmanned spacecraft and other aerospace applications often operate in environments that include other critical components, such as other electronic components and/or optical components. These other components may be highly sensitive to contaminants and may become inoperable if outgassing products from the adhesive materials deposit on the surfaces of these other components. Furthermore, these operating environments are typically enclosed and/or have low pressures (e.g., less than atmospheric pressure), which may cause more outgassing of the adhesive materials and more severe problems. As such, cured adhesive materials for unmanned spacecraft applications should produce substantially no outgassing. For purposes of this disclosure, a material produces substantially no outgassing when its total mass loss is less than about 1% when tested in accordance with ASTM E 595, entitled "Standard Test Method for Total Mass Loss and Collected Volatile Condensable Materials from Outgassing in a Vacuum Environment." The test is completed at 125° C. for 24 hours under a 5×10⁻⁵ torr vacuum or better. Many adhesives that are not suitable for aerospace applications have high outgassing due to solvents, low molecular weight polymer, or excessive low molecular weight curing agents. The outgas data and other properties for various adhesives is provided in Table 1 below:

TABLE 1

| Material | Tg, C. | CTE, ppm/C. | | Shear strength, psi | Outgass, % | | | Storage Modulus, msi | | Loss Modulus, ksi | |
|---|---|---|---|---|---|---|---|---|---|---|---|
| | | <Tg | >Tg | | TML | CVCM | VWR | <Tg | >Tg | <Tg | >Tg |
| Aptek 95402 | 37.5 | 26 | 89 | 2413 | 0.761 | 0.047 | 0.076 | 0.77 | 0.03 | 31 | 1.0 |
| 3M TC2810 | 93 | 70 | 197 | 2699 | 0.873 | 0.016 | 0.293 | 0.33 | 0.009 | 11 | 0.09 |
| Aptek 2311 | −77 | 35 | 133 | 434 | 0.662 | 0.019 | 0.299 | 0.69 | 0.02 | 27 | 1.5 |
| Arctic Silver | 52 | 39 | 124 | 1857 | 4.75 | 0.004 | 0.110 | 0.51 | 0.0003 | 14 | 0.3 |

Provided are adhesive materials capable of forming thermally conductive flexible bonds in electronic boards for use in unmanned spacecrafts and other aerospace applications. Also provided are methods of using these adhesive materials to form such bonds and methods of preparing these adhesive materials and various components thereof, such as treated filler particles. In some aspects, after curing, the adhesive materials have a thermal conductivity of at least about 2 W/m K and even at least about 2.5 W/m K for bonded joint configurations tested in vacuum. Furthermore, these thermal conductivity values are even higher than general thermally conductive adhesives that are not used for space applications (and deficient in some of the above listed characteristics, such as outgassing, glass transition temperature, and other characteristics). It should be noted that these thermal conductivity values correspond to bonded joint configurations tested in vacuum reflective of unmanned spacecraft and other aerospace applications.

The described adhesive materials may have a glass transition temperature of less than about −40° C. and, more specifically, less than about −60° C., such as about −70° C. Such a low glass transition temperature ensures that the operating temperature range does not overlap with the glass transition temperature thereby causing unexpected changes in mechanical properties during operation. Furthermore, these adhesive materials are sufficiently flexible and produce substantially no outgassing during their operation. In some aspects, the cured adhesive material has shear strength of between about 100 psi and 500 psi allowing the assemblies including these adhesives to be reworked without damaging remaining components of the assemblies. Furthermore, the tensile modulus of the cured adhesive may be between about $10^3$ psi and $10^5$ psi.

The described adhesive materials include filler particles and epoxies mixed together. The filler particles may be formed from boron nitride, aluminum nitride, and/or other suitable materials. The filler particles may have organofunctional groups on their surface to enhance bonding with the epoxies. For example, boron nitride particles may be treated with silane having organofunctional groups prior to combining these particles with a urethane modified epoxy. During curing the urethane modified epoxy may form covalent bonds with the organofunctional groups on the surface of the filler particles. The weight ratio of the particles in the adhesive material may be about 40-60% by weight. It has been experimentally determined that this weight ratio provides the maximum thermal conductivity while maintaining mechanical and other properties for unmanned spacecraft and other aerospace applications.

The filler particles may be combined with the epoxy using dual asymmetric centrifugal mixing. This type of mixing utilizes simultaneous rotation and revolution movement of a mixing container and, in some aspects, may be performed in a reduced pressure environment to eliminate introduction of air bubbles into the adhesive material. Furthermore, the dual asymmetric centrifugal mixing allows mixing of viscous materials without requiring dilution. In some aspects, the viscosity of the mixed adhesive material is at least about 100,000 cP or, more specifically, at least about 500,000 cP. High-viscosity mixing capabilities allow large weight ratios of filler particles and, in some aspects, provide higher shear forces during mixing to ensure adequate dispersion of the filler in the epoxy.

The described adhesive materials allow exploring new designs that have been previously limited by various power density constraints. For example, designs with tighter packaging of the components and/or designs using more powerful electronic components may become available. Furthermore, additional functionality of the existing electronic components may be explored. For example, some components may be operated at higher frequencies and/or draw more power. Currently, capabilities of some components are purposely limited to prevent overheating of these components. In a particular example, the payload electronic currently may use 2 W rated components that are operated at 0.5 W due to the limited heat dissipation capabilities with the currently used adhesives.

Examples of Electronic Assemblies Including Adhesive Materials

Prior to describing methods of forming thermally conductive flexible bonds and methods of preparing adhesive materials to form these bonds, a brief description of electronic assemblies used for unmanned spacecrafts and other aerospace applications is presented to provide better understanding of various features. Specifically, FIG. 1 is a schematic illustration of an assembly 100 including a cured thermally conductive flexible adhesive 106 that bonds an electronic component 108 to surface 104 of an electronic board 102. Electronic Board 102 may be installed on an unmanned spacecraft (e.g., Boeing 702HP, 702MP and 702SP spacecrafts). Examples of electronic components include resistors, transistors, diodes, capacitors, and other like devices. Electronic board 102 may be made from polyimide and epoxy resins.

Cured adhesive 106 may form a layer on surface 104 of electronic board 102. The layer may be a continuous layer or a patched layer. Specifically, the continuous layer may extend over surface 104 of electronic board 102 and extend in between adjacent electronic components on this electronic board 102. On the other hand, the patched layer may only cover individual areas corresponding to footprints of electronic components. The patched layer may not extend in between adjacent electronic components. The average thickness of this layer may be between about 0.001 inches and 0.010 inches or, more specifically, between about 0.004 inches and 0.008 inches, such as between about 0.005 inches and 0.006 inches. This thickness covers various topographical variations on surface 104 of electronic board 102 and allows some separation between the electronic component and the electronic board 102 (e.g., to prevent electrical shorts). At the same time, an excessive thickness increases the thermal resistance of this interface and adds to the overall weight of assembly 100.

In the final assembly, cured adhesive 106 directly contacts both electronic board 102 and electronic component 108 thereby providing a path for a heat flux between electronic board 102 and electronic component 108. In some aspects, cured adhesive 106 may partially or fully encapsulate some electronic components. For example, an electronic component may at least partially protrude into the layer formed by cured adhesive 106. Alternatively, an electronic component may have only a surface contact with a layer of cured adhesive 106 without protruding into the layer.

The characteristics of cured adhesive 106, such as its low shear strength (e.g., less than 500 psi), may allow removal of electronic component 108 from assembly 100 and replacing this original component with another component. For example, an original component may fail during testing or operation of assembly. This component may be electrically disconnected from electronic board 102 and then mechanically separated from cured adhesive 106 without disturbing other components of the assembly. An additional uncured adhesive material may be then introduced into this location and, when cured, may form a thermally conductive flexible bond with the remaining cured adhesive and a new electronic component.

Processing Examples

Figure 2A:
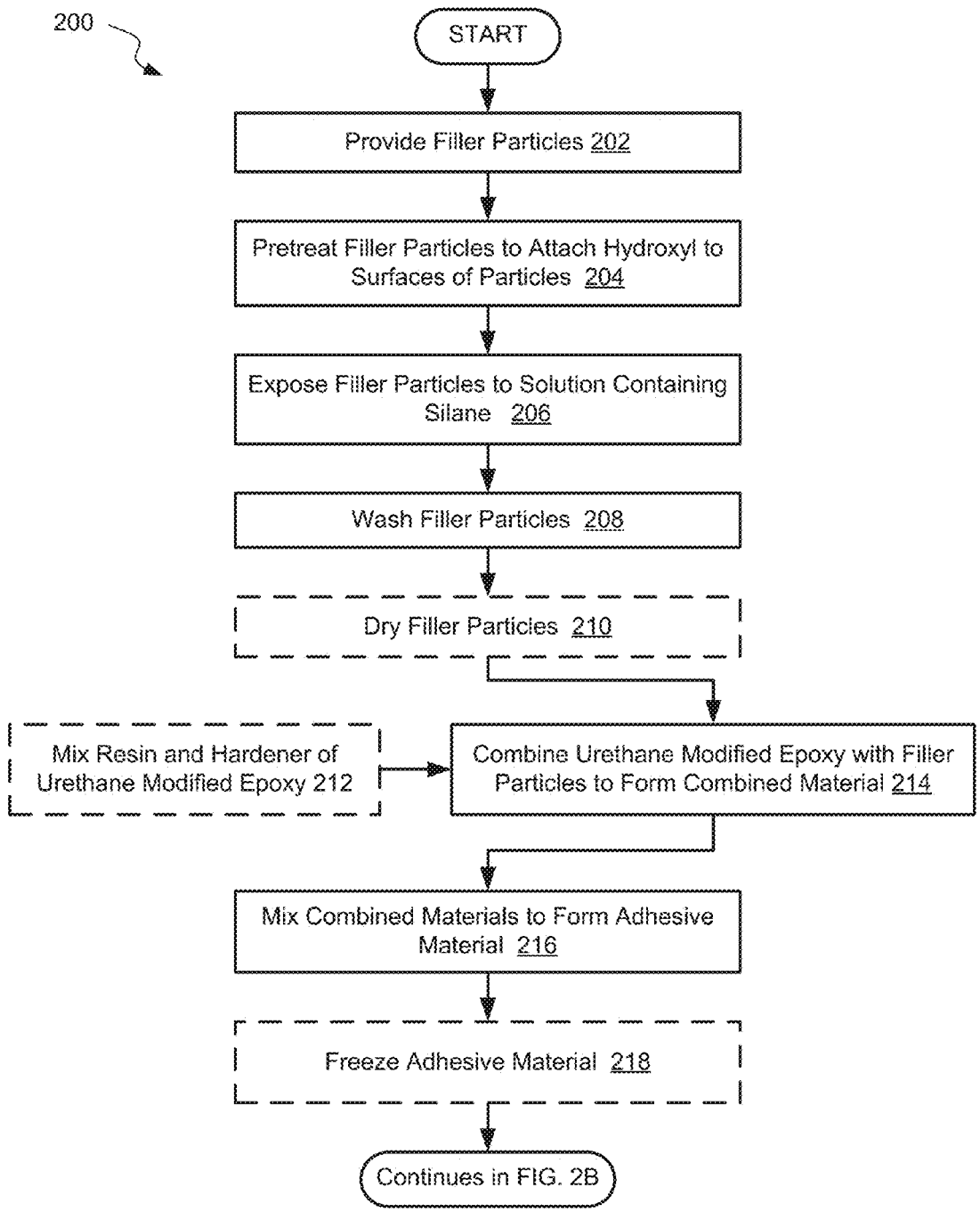
FIGS. 2A-2B illustrates a process flowchart corresponding to a method of forming a thermally conductive flexible bond for use in an electronic board of an unmanned spacecraft diagram, which includes a method of preparing a thermally conductive flexible adhesive material and components used in this adhesive material, in accordance with some aspects.
Figure 2B:
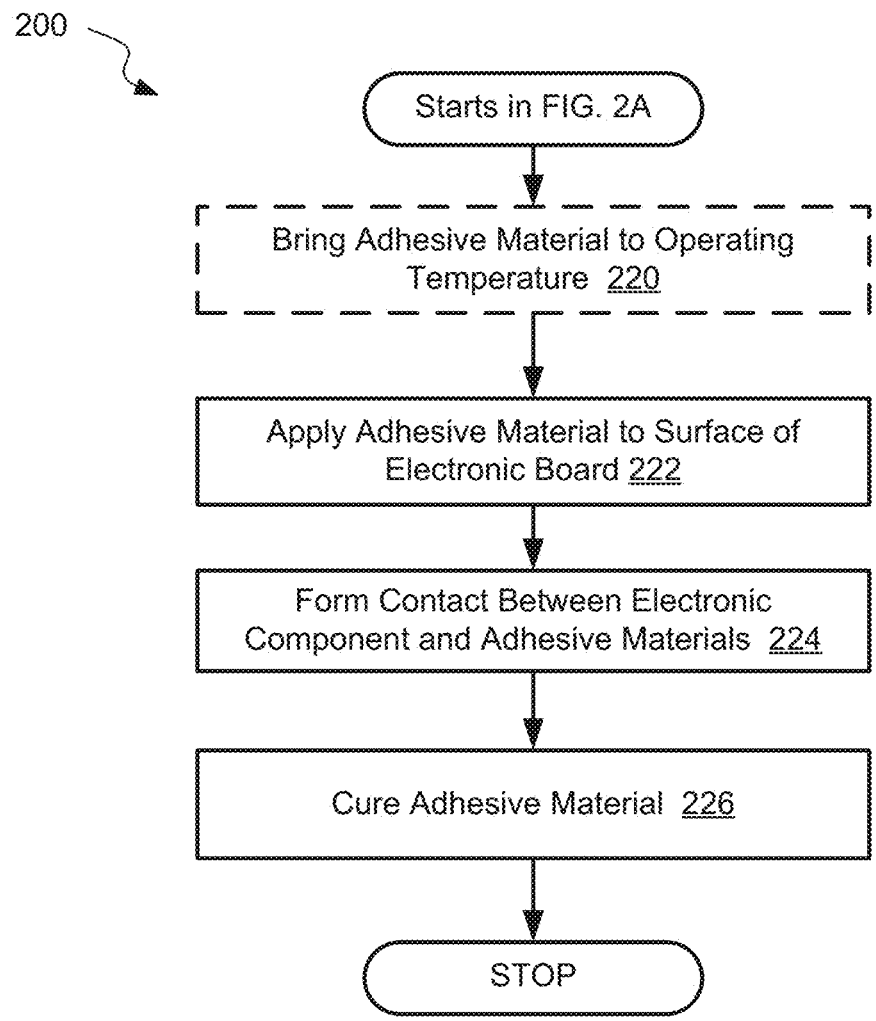

FIGS. 2A and 2B illustrate a process flowchart corresponding to a method 200 of forming a thermally conductive flexible bond for use in an electronic board of an unmanned spacecraft and other aerospace applications, in accordance with some aspects. The thermally conductive flexible bond is formed using a thermally conductive flexible adhesive material, which is often referred herein to as an adhesive material. In some aspects, a method of preparing a thermally conductive flexible adhesive material and/or components thereof is also a part of method 200. Alternatively, a previously prepared adhesive material may be used in method 200 without any upstream operations. For example, a frozen pre-mix may be provided, and method 200 may commence with operation 220 during which the frozen pre-mix is brought to an operating temperature.

Furthermore, a method of preparing a thermally conductive flexible adhesive may be performed without a subsequent use of this adhesive by the same entity. For example, treated filler particles may be provided, and method 200 may commence with operation 212 and/or operation 214 during which the treated filler particles are combined with an epoxy to eventually form an adhesive material. This adhesive material may be used right away in operations 222-226 to form conductive flexible bonds or may be frozen during operation 218 and stored to be used by the same or different entity.

Furthermore, one or more components of a thermally conductive flexible adhesive material may be prepared using various operations described herein. These components may be used in a subsequent method (e.g., by another entity) to prepare the adhesive material. For example, filler particles may be treated during operations 202-210 and then stored for future use by the same or different entity.

Overall, method 200 described herein with reference to FIGS. 2A and 2B may include different groups of operations performed independently from each other by the same entity or by different entities. As such, not all operations presented in FIGS. 2A and 2B need to be a part of the same method.

In some aspects, method 200 may commence with providing filler particles during operation 202. The filler particles may be formed from boron nitride, aluminum nitride, aluminum oxide, and combinations thereof. In general, materials having a high thermal conductivity and a low electrical conductivity may be used as fillers for thermally conductive flexible adhesive materials described herein. However, as notes above, most materials with high thermal conductivities are also good electrical conductors and, therefore, are not suitable as fillers. In some aspects, the filler particles are formed from boron nitride. Boron nitride has a thermal conductivity of about 300 W/(m-K) (in the a-b plane of the crystal), while its electrical resistivity is greater than about $10^{14}$ Ohm-cm. In some aspects, the filler particles are formed from aluminum nitride. Aluminum nitride has a thermal conductivity of up to 140-180 W/(m-K), while its electrical resistivity is greater than about $10^{14}$ Ohm-cm. Of course, these properties may depend on purity, morphology, and other characteristics of the material.

The filler particles may be in a form of agglomerates, spheres, and platelets. In general, the shape of the filler particles may be described as a three-dimensional shape, such that an average aspect ratio between any two dimensions of the filler particles is less than 5. The three-dimensional shape should be distinguished from a one-dimensional shape, in which one dimension substantially exceeds (by more than 5 times) the two other dimensions. Some examples of the one-dimensional shape include wires, rods, fibers, and the like. The three-dimensional shape should be distinguished from a two-dimensional shapes, in which each of two dimensions substantially exceeds (by more than 5 times) the remaining dimension. Some examples of the two-dimensional shape include flakes, platelets, and the like. This understanding has been experimentally verified. Unlike the two dimensional particles or the one-dimensional particles, three-dimensional particles have comparable thermal conductivities in all three dimensions.

Figure 4A:
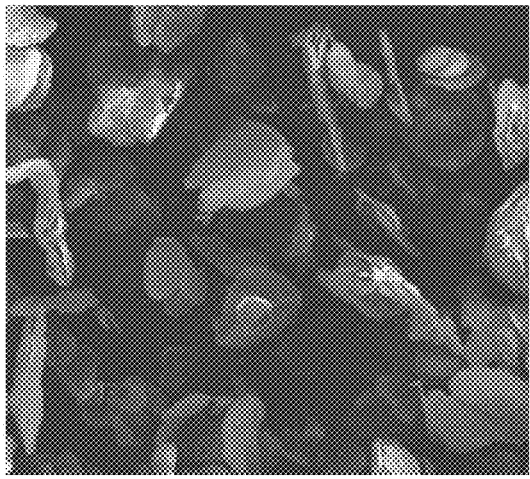
FIG. 4A-4D are scanning electron microscope (SEM) photos of different filler particles.
Figure 4B:
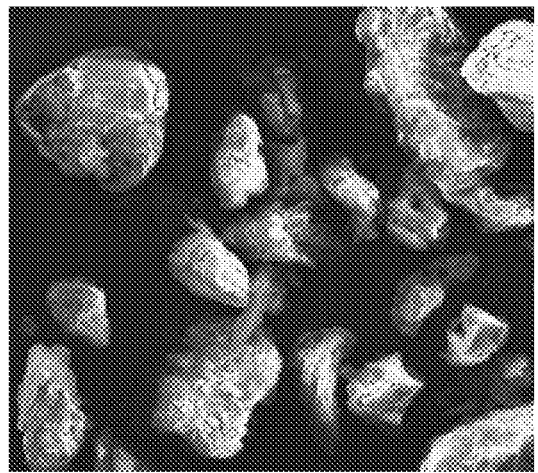
Figure 4C:
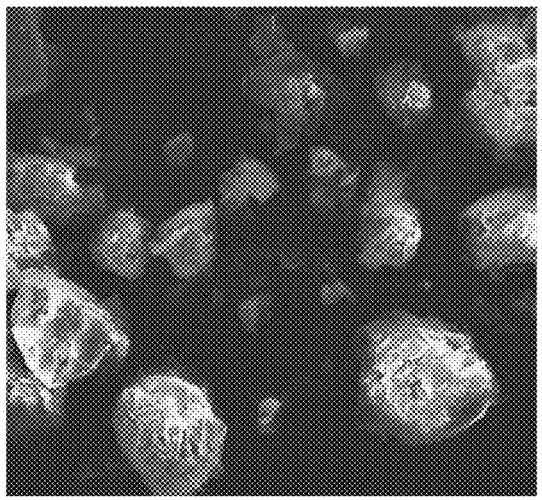
Figure 4D:
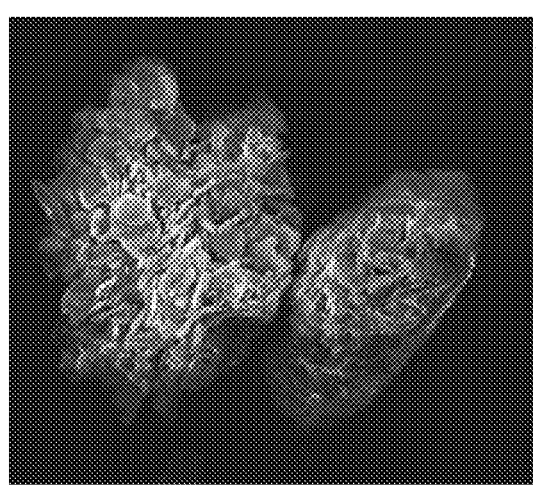

Specific examples of filler particles include PT350 boron nitride particles and PTX60 boron nitride particles, both supplied by Momentive Performance Materials in Columbus, Ohio. PT350 particles have a mean particle size of 125-150 micrometers, a surface area of 3.3 m²/g, and the tap density of 0.7 g/m³. PTX60 particles have a mean particle size of 55-65 micrometers, a surface area of 5.5 m²/g, and the tap density of 0.4 g/m³. An SEM image of PT350 particles is presented in FIG. 4D, while an SEM image of PTX60 particles is presented in FIG. 4C. PT350 particles maybe characterized as medium-density agglomerates, while PTX60 particles maybe characterized as spherical agglomerates.

Other examples of filler particles include PCTP30 boron nitride particles and PCTH3MHF boron nitride particles, both supplied by Saint-Gobain Ceramic Materials in Amherst, N.Y. PCTP30 particles have a mean particle size of 75 micrometers, a surface area of 2.5 m²/g, and the tap density of 0.8 g/m³. PCTH3MHF particles have a mean particle size of 30 micrometers, a surface area of 2.5 m²/g, and the tap density of 0.6 g/m³. An SEM image of PCTP30 particles is presented in FIG. 4A, while an SEM image of PCTH3MHF particles is presented in FIG. 4B. PCTP30 particles maybe characterized as high-density agglomerates, while PCTH3MHF particles maybe characterized as platelets.

In some aspects, the average particle size of the filler is between about 10 micrometers and 200 micrometers or, more specifically, between about 20 micrometers and 120 micrometers, such as between 50 micrometers and 150 micrometers. Similar to the shape of the filler particles, these dimensions provide a specific combination of thermal and mechanical properties as further described below. Specifically, these dimensions allow achieving a desirable packing density to provide a good thermal conductivity while retaining sufficient bonds between materials to maintain mechanical properties.

Figure 3D:
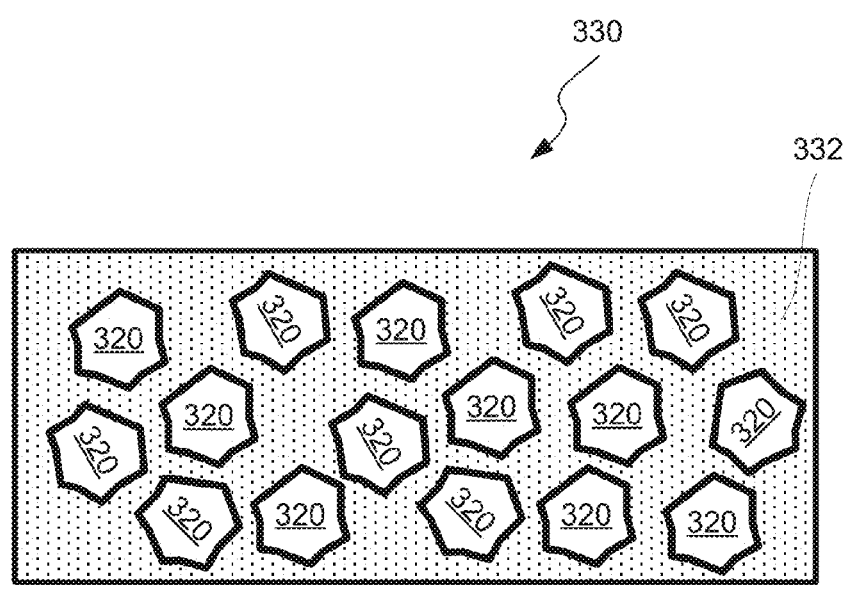
FIG. 3D is a schematic illustration of a thermally conductive flexible adhesive material formed using the treated particles, in accordance with some aspects.

Method 200 may proceed with pretreating the filler particles to attach hydroxyl groups to a surface of these particles during operation 204. For example, the filler particles may be treated in a high humidity environment, such as at a temperature 85° C. and 85% relative humidity for four hours. The pretreated filler particles have demonstrated a much higher adsorption of silane on their surface as shown in the experimental results section below. FIG. 3A is a schematic illustration of a filler particle 300 prior to operation 204, while FIG. 3B is a schematic illustration of a filler particle 310 after operation 204 showing hydroxyl groups attached to the surface.

Method 200 may proceed with exposing the filler particles to a silane containing solution during operation 206. Hydrolyzable groups of silane undergo hydrolysis and condensation reactions as shown by the following two reactions:

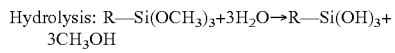

Hydrolysis: R—Si(OCH₃)₃+3H₂O→R—Si(OH)₃+ 3CH₃OH

Condensation:

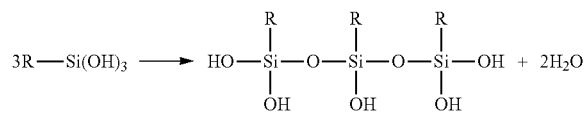

After the condensation reaction, the hydroxyl groups of the modified silane form hydrogen bonds with the hydroxyl groups on the surface of the filler particles and may eventually form covalent bonding following the release of water. A schematic representation of a resulting structure is shown in FIG. 3C. Specifically, structure 320 includes a filler particle 300 and covalently bound functional groups (R). In some aspects, these functional groups are organofunctional groups, such as epoxide groups (e.g., C₂OH₃R) or, more specifically, glycidyl groups, which include both epoxide and alcohol functional groups (e.g., C₂OH₃R, where R is O(CH₂)ₙ, n=1-5 or, more specifically, n=2-4, such as n=3). A silane-containing solution used in operation 206 may also include a solvent. It has been found that some solvents, such as water, are more effective in forming bonds between silane and filler particles than others, such as methanol and isopropyl alcohol. A series of tests were conducted to determine effectiveness of different solvents. For example, it has been found that effectively no silane was retained on the surface of boron nitride particles when methanol or isopropyl alcohol was used to dissolve (3-glycidyloxypropyl) trimethoxysilane as further described below.

Furthermore, it has been found that acidity of the solution effects ability of silane to bind to the surface of the filler particles. For example, no silane was bound to the surface of boron nitride particles when these particles were treated in a water-based solution of (3-glycidyloxypropyl)trimethoxysilane having a pH level of 3. Also, much less silane was retained on the surface when the pH level was increased above a pH level of 6. In some aspects, the solution has a pH level of between about 5 and 6. The solution may be a water-based solution in these aspects.

The binding of silane to the surface of the filler particles may be also impacted by the concentration of silane in the solution used during operation 206. In some aspects, the concentration of silane relative to the weight of the filler particles (in this solution) is between about 1.5% by weight and 4% by weight or, more specifically, between about 2% by weight and 3% by weight. Experiments have shown that 2.4% weight ratio of (3-glycidyloxypropyl) trimethoxysilane to boron nitride resulted in more silane bound to boron nitride particles than a 1.2% or a 4.8%. Too much silane may cause excessive cross-linking (polymerization) on the surface of the particles resulting in agglomeration of the particles. At the same time insufficient amounts of silane do not provide enough binding between the particles and the epoxy. It should be noted that while other components may be present in a solution used for treating filler particles with silane, the weight ratios of silane are relative to the weight of the filler particles unless other references are specifically stated.

In some aspects, method 200 may involve washing the filler particles during operation 208. The washing operation removes residual silane that is not bound to the filler particles. For example, the treated particles may be mixed one or more times with water or some other suitable liquid. Method 200 may also involve an optional drying operation 210 during which residual solvent may be removed from the treated particles. In some aspects, the particles may be introduced into subsequent operations with some residual solvent remaining if, for example, the solvent is compatible with an epoxy used to form an adhesive material.

As noted above, method 200 may stop before operations 212 and 214 (e.g., after completing operation 208 or operation 210). The treated filler particles may be stored at this point. In some aspects, the treated particles are transferred to another entity for further processing. Alternatively, method 200 may proceed with operations 212 and 214.

During operation 214 an epoxy or some other type of a base adhesive material is combined with treated particles thereby forming a combined material. A specific example of a base adhesive material is a urethane modified epoxy. Polyurethanes, epoxies, and silicones, and urethane modified epoxy may include two components, such as a resin and a hardener. The urethane modified epoxy used may be a low-modulus, low-glass transition temperature epoxy. Without adding filler particles (e.g., as a cured base adhesive material), the urethane modified epoxy may have a low glass transition temperature (e.g., less than −60° C., such as about −80° C.) and low shear strength (e.g., less than 500 psi).

When a multi-component base adhesive material is used during operation 214, the treated particles may be combined with one or both of these components. For example, the resin and hardener of an epoxy may be first mixed during optional operation 212 and then this mixture may be combined with the treated particles during operation 214. The resin and hardener may be mixed using a dual asymmetric centrifugal mixer or another type of mixer. When the dual asymmetric centrifugal mixer is used the mixing duration may be between about 15 seconds and 60 seconds, such as about 30 seconds. The rotation speeds may be between about 1000 RPM and 5000 RPM, such as about 3000 RPM. At 3000 RPM rotation about the main axis of the mixer, the container also rotates at 750 rpm around its own center axis. Overall, operation of the dual asymmetric centrifugal mixer will be readily understood by one having ordinary skills in the art.

Mixing the resin and hardener (prior to introducing the treated particles) reduces the viscosity of the mixture and allows introducing more treated particles than otherwise possible. In some aspects, the concentration (weight loading level) of the treated particles in the combined material formed during operation 214 is between about 20% by weight and 70% by weight or, more specifically, between about 40% by weight and 60% by weight relative to the total amount of the combined material. These loading levels depend on the type of types, sizes, morphology and other characteristics of the filler particles.

Furthermore, mixing the resin and hardener (prior to introducing the treated particles) allows reducing the mixing time needed for a mixture containing the treated particles and, therefore, reducing the overall stress experienced by these particles. It has been found that excessive mixing of materials containing particles tend to change the shape and size of these particles. As a result, the thermally conductive characteristics of resulting adhesive material are often negatively impacted. For example, smaller particles may have less contact between the particles than larger particles for the same weight loading. In some aspects, the total mixing time, after the treated particles are introduced into the mixture, is less than 5 minutes or, more specifically, less than 2 minutes, or even less than 1 minute. In some aspects, mixing is performed in stages with one or more cooling breaks in between the mixing stages. Controlling the temperature helps to reduce curing of the mixture at that stage. Other cooling techniques (such as using a cooling jacket on a mixing container) can be used as well for this temperature control. For example, the temperature of the mixture may be kept below 60° C. or, more specifically, below 50° C. during operation 214.

In some aspects, the treated particles may be combined with either the resin or the hardener but not both during operation 214. In other words, operation 212 is not performed. In some aspects, a portion of the treated particles may be combined with the resin and another portion of the treated particles may be combined with the hardener. However, these two portions may not be combined with each other until operation 214. These approaches eliminate the contact between the resin and hardener and not initiate the curing process until later processing stages.

Method 200 may proceed with mixing the combined material to form a thermally conductive flexible adhesive material during operation 216. The mixed adhesive material has a uniform distribution of the resin, the hardener, and the treated particles within the material unlike, for example, the combined material at the end of operation 214. After operation 216, the adhesive material may be ready for use or may be stored, for example, by freezing the adhesive during optional operation 218. If the adhesive material is frozen, it may be brought back to an operating temperature (e.g., a room temperature) during operation 220.

Operation 216 may involve mixing the combined material using a dual asymmetric centrifugal mixer or another suitable mixer. In some aspects, the rotational speed of the dual asymmetric centrifugal mixer is between about 1000 RPM and 2000 RPM or, more specifically between about 1400 RPM and 1600 RPM. The lower speeds for this operation (as opposed the operation used to pre-mix the resin and the hardener) is used to avoid grinding down the filler particles. The thermally conductive flexible adhesive may have a viscosity of at least about 100,000 cP after mixing or even at least about at least about 500,000 cP.

Method 200 may proceed with applying the adhesive material to a surface of an electronic board during operation 222 and forming a contact between an electronic component and the adhesive materials during operation 224. The adhesive material is then cured during operation 226. The curing operation may involve thermal curing, for example, by heating the assembly including the adhesive to less than about 110° C., such as to about 100° C., for about 1 hour. Many conventional electronic-grade adhesives need curing temperatures of at least 120° C., which may be damaging for components of unmanned spacecrafts. It should be mentioned that adhesives containing fillers and adhesive used for applications that does not allow direct line of sight generally cannot be cured using exposure methods, such as UV curing, IR curing, X-Ray curing, and other like curing.

Experimental Results

Various experiments were conducted to characterize performance of different filler particles. Specifically, PT350 particles, PTX60 particles, PCTP30 particles, and PCTH3MHF particles were tested. Some description and characteristics of these particles are presented above. In one test, a maximum possible weight loading of these four types of particles was tested using two epoxies, e.g., Aptek 95318, which has a glass transition temperature of less than −60° C. and is a urethane modified epoxy system, and Aptek 95143, which has a lower viscosity than Aptek 95318 but has a higher glass transition of about 50° C. and is an epoxy system. Maximum loading is determined when the paste is no longer spreadable on bare aluminum and/or based on a maximum extrusion rate. PT350 particles had a maximum weight loading of about 62% in both epoxies, while PTX60 particles had a maximum weight loading of about 50% in both epoxies. The average maximum loading was about 67% for both for PCTP30 particles and PCTH3MHF particles. In general, the highest possible loading is needed. However, there is a tradeoff between the maximum loading, paste usability, and strength.

Another test was conducted to determine thermal conductivities of cured adhesive materials prepared using 30% weight loading of the same four types of filler particles. A bonded joint configuration in vacuum was used. Various aspects of this test are described above. A 5 mil bond line was controlled by adding 0.005" diameter glass beads. No bondline had no control resulting in filler particle size (minor factor) and adhesive viscosity (major factor) controlling the bondline. The test results are presented in TABLE 2A below.

TABLE 2A

| Thermal Conductivity (W/m K) at 30% Weight Loading | | |
|---|---|---|
| Particles | 5 mil Bond Line | No Bond Line |
| PCTP30 | 0.65 | 0.10 |
| PCTH3MHF | 0.45 | 0.38 |
| PT350 | 0.79 | 1.05 |
| PTX60 | 0.64 | 0.98 |

The thermal conductivity test was repeated for the same four types of filler particles (e.g., the PT350 particles, PTX60 particles, PCTP30 particles, and PCTH3MHF particles) at their maximum loadings. Again, a bonded joint configuration in vacuum was used. The test results are presented in TABLE 2B below.

TABLE 2B

Thermal Conductivity (W/m K) at the Maximum Weight Loadings

| Particles | Maximum Loading | 5 mil Bond Line | No Bond Line |
|---|---|---|---|
| PCTP30 | 52% wt | 1.25 | 0.35 |
| PCTH3MHF | 55% wt | 1.15 | 1.55 |
| PT350 | 41% wt | 1.49 | 3.90 |
| PTX60 | 52% wt | 2.40 | 2.35 |

Yet another thermal conductivity test was conducted for various combinations of the PCTP30 particles and PCTH3MHF particles and, separately, for various combinations of the PT350 particles and PTX60 particles. The total loading for these combinations was set at 30% by weight. The test results are presented in TABLE 3 and TABLE 4 below.

TABLE 3

Thermal Conductivity (W/m K) of Combinations of Two Types of Particles

| PCTP30 Ratio | PCTH3MHF Ratio | 5 mil Bond Line |
|---|---|---|
| 0% wt | 100% wt | 0.48 |
| 25% wt | 75% wt | 0.50 |
| 50% wt | 50% wt | 0.42 |
| 75% wt | 25% wt | 0.47 |
| 100% wt | 0% wt | 0.66 |

TABLE 4

Thermal Conductivity (W/m K) of Combinations of Two Types of Particles

| PT350 Ratio | PTX60 Ratio | 5 mil Bond Line |
|---|---|---|
| 0% wt | 100% wt | 0.65 |
| 25% wt | 75% wt | 0.66 |
| 50% wt | 50% wt | 0.81 |
| 75% wt | 25% wt | 0.72 |
| 100% wt | 0% wt | 0.79 |

Based on the above experimental results, PTX60 particles demonstrated the best performance followed by PT350 particles. The surface area is believed to be the key factor in this test.

Additional tests were performed to determine parameters for treating the surface of filler particles. The goal of this treatment was to increase compatibility and wettability of particles with test epoxies. One compatibility aspect was to reduce a viscosity of the mixed adhesive material. Another aspect was establishing bonds between filler particles and epoxies. Specifically, a silane treatment using (3-glycidyloxypropyl) trimethoxysilane was used. The silane treatment followed by thermal gravimetric analysis (TGA), which involves heating the treated filler particles to 600° C. to decompose and remove most of the silane on the surface of the treated particles and to measure the weight loss as a result of this silane decomposition and removal.

To ensure bonding of silane to the surface of filler particles, the surface was pre-treated to introduce hydroxyl groups as described above. Four different samples were subjected to the thermal gravimetric analysis. The first sample included particles that were not exposed to silane at all (e.g., the first reference). This sample demonstrated only 0.08% weight loss attributed to non-silane losses/noise. The second sample included particles that were exposed to silane but were not pre-treated (e.g., the second reference). This sample demonstrated about 0.2% weight loss. The third sample included particles that were pretreated using sodium hydroxide and then exposed to silane. This sample demonstrated about 0.1% weight loss. This value was not significantly greater than the value for the first reference and in fact was worse than the second reference. Finally, the fourth sample included particles that were pretreated in a humid environment (e.g., environment containing a high concentration of water vapor) and then exposed to silane. This sample demonstrated about 0.26% weight loss.

In another test different solvents were tested for a silane-containing solution. (3-glycidyloxypropyl) trimethoxysilane was combined with different solvents followed by treatment of the particles. Methanol and isopropanol demonstrated roughly the same performance as a reference sample that was not treated, which was less than 0.075% weight loss. However, when water was used to dissolve silane, the weight loss of the treated filler particles went up to 0.26%.

Another test was conducted to determine effects of acidity of the silane containing solution on binding of silane to the filler particles. The pH levels from 3 to 8.5 were tested. The results of this test are presented in TABLE 5 below.

TABLE 5

TGA Weight Loss as a Function of Solution Acidity

| pH of Solution | TGA Weight Loss |
|---|---|
| Reference (No Treatment) | 0.075% |
| 3 | 0.09% |
| 5.5 | 0.26% |
| 7 | 0.22% |
| 8.5 | 0.21% |

Yet another test was conducted to determine effects of the silane concentration on retention of the silane on the filler particles. Solutions with silane concentrations from 0% to 4.8% by weight based on the weight of filler particles treated in these solutions were prepared, and the boron nitride particles were independently treated in each of these solutions. The results of this test are presented in TABLE 6 below.

TABLE 6

TGA Weight Loss as a Function of Silane Concentration

| Silane Concentration, by weight | TGA Weight Loss |
|---|---|
| Reference (No Treatment) | 0.075 |
| 0% (Solvent Only) | 0.075 |
| 1.2% | 0.16 |
| 2.4% | 0.26 |
| 4.8% | 0.13 |

Examples of Aircraft

Figure 5A:
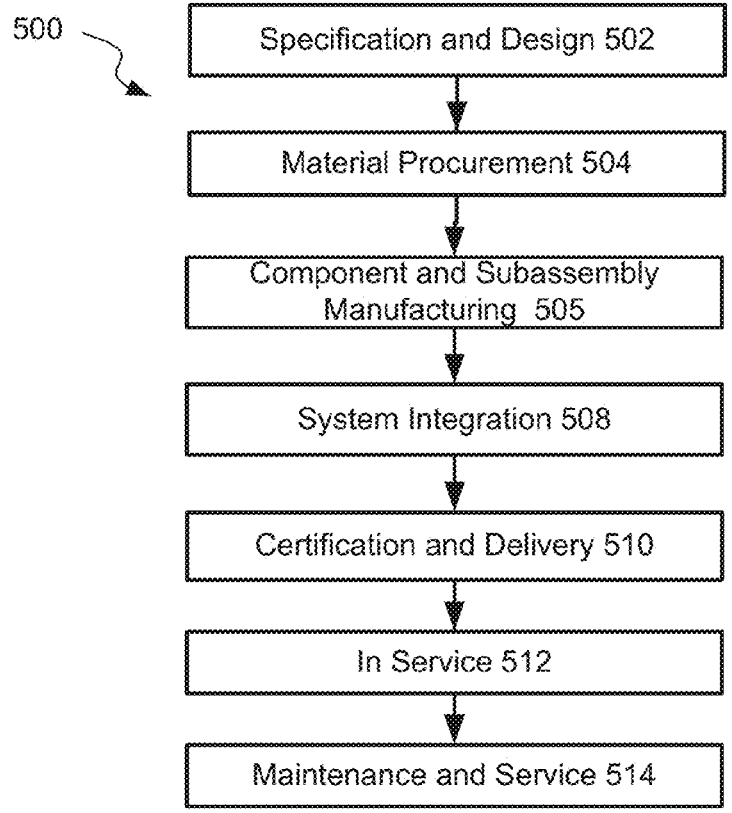
FIG. 5A is a process flowchart reflecting key operations in the life cycle of an aircraft from early stages of manufacturing and to entering service, in accordance with some aspects.
Figure 5B:
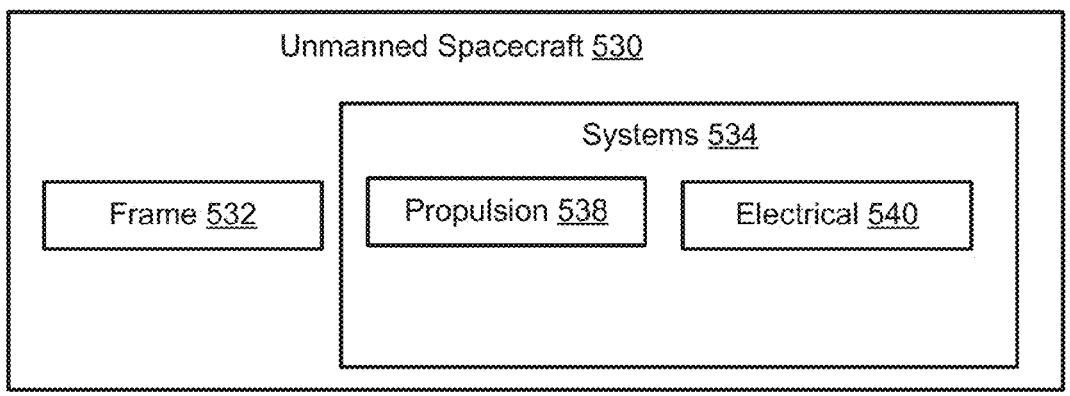
FIG. 5B is a block diagram illustrating various key components of an aircraft, in accordance with some aspects.

FIG. 5A is a general flowchart of manufacturing and service method 500 for various vehicles, aircraft, and spacecraft. While the description below refers to unmanned spacecrafts, one having ordinary skills in the art would understand that similar operations and general components may be used for other vehicles, such as aircraft. FIG. 5B is a general block diagram of an unmanned spacecraft and will now be described to better illustrate various features of processes and systems presented herein.

During pre-production, unmanned spacecraft manufacturing and service method 500 may include specification and design 502 of unmanned spacecraft 530 and material procurement 504. The production phase involves component and subassembly manufacturing 505 and system integration 508 of unmanned spacecraft 530. Thereafter, unmanned spacecraft 530 may go through certification and delivery 510 in order to be used in service 512 (e.g., for a specific space mission). While in service, unmanned spacecraft 530 may be scheduled for routine maintenance and service 514 (which may also include modification, reconfiguration, refurbishment, and so on).

Each of the processes of unmanned spacecraft manufacturing and service method 500 may be performed or carried out by a system integrator, a third party, and/or an operator (e.g., a customer). For the purposes of this description, a system integrator may include, without limitation, any number of unmanned spacecraft manufacturers and major-system subcontractors. A third party may include, for example, without limitation, any number of venders, subcontractors, and suppliers.

As shown in FIG. 5B, unmanned spacecraft 530 produced by aircraft manufacturing and service method 500 may include frame 532, and multiple systems 534. Some examples of systems 534 include one or more of propulsion system 538 and electrical system 540. Electrical system 540 may be fabricated and/or services using one or more of thermally conductive flexible adhesive materials and methods described above.

Apparatus and methods disclosed herein may be employed during any one or more of the stages of manufacturing and service method 500. Also, one or more apparatus aspects, method aspects, or a combination thereof may be utilized during component and subassembly manufacturing 505 and system integration 508, for example, without limitation, by substantially expediting assembly of or allowing new features (e.g., electronic circuit designs) of unmanned spacecraft 530. Similarly, one or more of apparatus aspects, method aspects, or a combination thereof may be utilized while unmanned spacecraft 530 is in service, for example, without limitation, to maintenance and service 514 may be used during system integration 508 and/or maintenance and service 514 to determine whether parts may be connected and/or mated to each other.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present aspects are to be considered as illustrative and not restrictive.

What is claimed is:

1. A method of preparing a thermally conductive flexible adhesive material, the method comprising:
   providing boron nitride particles,
      wherein an average aspect ratio between any two dimensions of the boron nitride particles is less than 5,
      wherein an average particle size of the boron nitride particles is between 10 micrometers and 200 micrometers;
   attaching hydroxyl groups to a surface of the boron nitride particles;
   exposing the boron nitride particles having the hydroxyl groups on the surface to a solution comprising silane thereby attaching organofunctional groups of the silane to the surface of the boron nitride particles; and
   washing the boron nitride particles having the organofunctional groups on the surface to remove residual silane.

2. The method of claim 1, wherein the organofunctional groups are glycidyl groups.

3. The method of claim 1, wherein the silane comprises (3-glycidyloxypropyl) trimethoxysilane.

4. The method of claim 1, wherein the solution has a pH level of between 5 and 6.

5. The method of claim 1, wherein a concentration of the silane to boron nitride is between 2% by weight and 3% by weight.

6. The method of claim 1, further comprising, after washing the boron nitride particles,
   combining a urethane modified epoxy with boron nitride particles thereby forming a combined material, and
   mixing the combined material to form the thermally conductive flexible adhesive material.

7. The method of claim 6, wherein a concentration of the boron nitride particles in the combined material is between 40% by weight and 60% by weight.

8. The method of claim 6, wherein mixing the combined material is performed using a dual asymmetric centrifugal mixer.

9. The method of claim 6, further comprising freezing the thermally conductive flexible adhesive material.

10. The method of claim 6, further comprising
    applying the adhesive material onto a surface of an electronic board;
    forming a contact between an electronic component and the adhesive material applied to the surface of the electric board; and
    curing the adhesive material thereby forming a cured adhesive structure between the electric board and the electronic component,
       wherein the cured adhesive structure provides a thermally conductive flexible bond between the electric board and the electronic component.

11. The method of claim 1, wherein the organofunctional groups further comprise alcohol functional groups.

12. The method of claim 1, wherein the organofunctional groups are represented by $C_2OH_3R$, where R is $O(CH_2)_n$ and where n is between 1 and 5.

13. The method of claim 1, wherein the organofunctional groups are represented by $C_2OH_3R$, where R is $O(CH_2)_n$ and where n is between 2 and 4.

14. The method of claim 1, wherein the organofunctional groups are covalently bound to the surface of the boron nitride particles.

* * * * *